United States Patent
Dalal et al.

(10) Patent No.: US 9,702,815 B2
(45) Date of Patent: Jul. 11, 2017

(54) SAMPLING DEVICE AND METHODS OF USING SAME

(71) Applicant: Boehringer Ingelheim Roxane, Inc., Columbus, OH (US)

(72) Inventors: Atish Dalal, Powell, OH (US); Daniel Hill, Springfield, OH (US)

(73) Assignee: BOEHRINGER INGELHEIM ROXANE, INC., Columbus, OH (US)

( * ) Notice: Subject to any disclaimer, the term of this patent is extended or adjusted under 35 U.S.C. 154(b) by 0 days.

(21) Appl. No.: 14/535,687

(22) Filed: Nov. 7, 2014

(65) Prior Publication Data

US 2015/0129764 A1 May 14, 2015

Related U.S. Application Data

(60) Provisional application No. 61/902,554, filed on Nov. 11, 2013.

(51) Int. Cl.
| | |
|---|---|
| *G01J 1/42* | (2006.01) |
| *G01N 21/3563* | (2014.01) |
| *G01N 21/359* | (2014.01) |
| *G01N 21/85* | (2006.01) |

(52) U.S. Cl.
CPC ....... *G01N 21/3563* (2013.01); *G01N 21/359* (2013.01); *G01N 21/8507* (2013.01)

(58) Field of Classification Search
CPC .... G01N 21/3563; G01N 21/359; G01N 1/12; G01J 3/51; G03B 27/58; A61B 1/005
See application file for complete search history.

(56) References Cited

U.S. PATENT DOCUMENTS

| | | | |
|---|---|---|---|
| 5,474,140 A | 12/1995 | Stevens | |
| 5,476,017 A | 12/1995 | Pinto et al. | |
| 5,694,206 A * | 12/1997 | Curtiss | G01N 21/8507 356/414 |
| 5,996,426 A * | 12/1999 | Robinson | B01L 3/02 73/864.45 |
| 6,393,926 B1 | 5/2002 | Bowersox, Jr. et al. | |
| 6,631,650 B1 | 10/2003 | Espinosa | |
| 2008/0249541 A1* | 10/2008 | Stokes | A61B 17/068 606/142 |
| 2011/0141448 A1* | 6/2011 | Aoki | B65G 49/064 355/72 |

FOREIGN PATENT DOCUMENTS

EP 1238255 9/2002

OTHER PUBLICATIONS

Chowhan, Zak T., Sampling of Particulate Systems, Pharmaceutical Technology, Apr. 1994, pp. 48-55.
(Continued)

*Primary Examiner* — Tarifur Chowdhury
*Assistant Examiner* — Jamil Ahmed
(74) *Attorney, Agent, or Firm* — Pearne & Gordon LLP

(57) ABSTRACT

A sampling device including a Near-Infrared Spectroscopy (NIRS) fiber optic probe and methods of using the device are provided. The sampling device performs both NIRS data collection and physical sample collection. The sampling device operates by inserting the device into a powder or blend to be sampled, collecting a sample within the sample chamber in the device, and performing NIRS analysis of the sample within the sample chamber.

18 Claims, 4 Drawing Sheets

(56) References Cited

OTHER PUBLICATIONS

Berman, et al., Blend Uniformity and Unit Dose Sampling, Drug Development and Industrial Pharmacy, 1995, vol. 21, No. 11, pp. 1257-1283, Marcel Dekker, Inc.
Hwang, et al., Evaluation of Blend Sampling Errors: A Statistical Approach; Pharmaceutical Technology, Jun. 1999, pp. 56-65.
Kaye, Brian H., Sampling and characterization research: Developing two tools for powder testing, Powder and Bulk Engineering, Feb. 1996, pp. 44-54.
Pastor, et al., A Novel Sample Thief Designed to Avoid Biased Data; Pharmaceutical Technology, 1999, Yearbook, pp. 47-54.
Muzzio, et al., An Improved Powder-Sampling Tool; Pharmaceutical Technology, Apr. 1999, pp. 92-110.
Carstensen, et al., Blending Validation and Content Uniformity of Low-Content, Noncohesive Powder Blends, Drug Development and Industrial Pharmacy, 1996, vol. 22, No. 4, pp. 285-290, Marcel Dekker, Inc.
Kraemer, et al., Sampling Bias in Blending Validation and a Different Approach to Homogeneity Assessment, Drug Development and Industrial Pharmacy, 1999, vol. 25, No. 2, pp. 217-222, Marcel Dekker, Inc.
Berman, et al., Unit Dose Sampling: A Tale of Two Thieves, Drug Development and Industrial Pharmacy, 1996, vol. 22, No. 11, pp. 1121-1132, Marcel Dekker, Inc.

\* cited by examiner

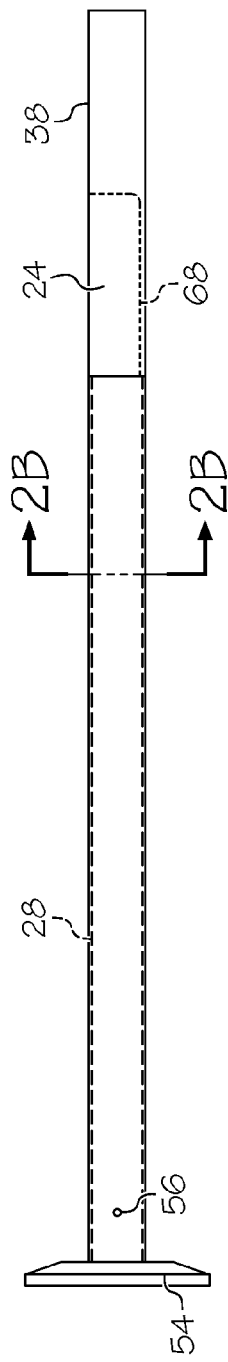
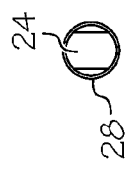
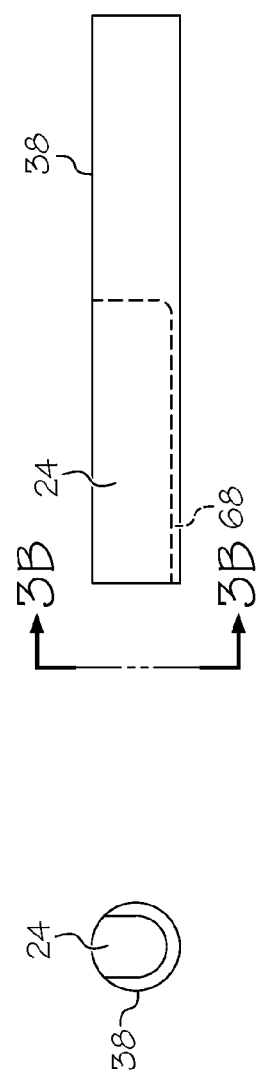
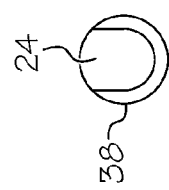

SAMPLING DEVICE AND METHODS OF USING SAME

FIELD

The present invention relates generally to sampling devices and methods of using sampling devices, and more particularly, sampling devices including a NIRS fiber optic probe and methods of using such devices.

BACKGROUND

Sampling devices are used to obtain blend samples, such as in manufacturing of pharmaceutical products. Sampling with a grain-type sampler device is typically performed by an operator (or a technician) inserting the sampler tip into the powder bed with the sample port closed. The sample port is then opened, and the sampler is agitated or pushed further into the powder bed to allow the powder sample to enter the sampler chamber. The sample port is then closed, and the sample is removed and dispensed into a suitable container. After dispensing the samples from the sampling device, the samples are often sent to a quality control laboratory to be analyzed. The quality control laboratory performs an analysis of the samples.

Analysis times typically vary from 24 hours to 7 days, depending on factors such as laboratory capacity and test methods. The forward processing of a sampled blend occurs after the quality control laboratory completes and releases its analysis of the sample taken. Thus, while a manufacturing facility waits for receipt of this data from the laboratory, the sampled blends are stored for several days, which can disadvantageously lead to particle segregation and de-mixing. This limits a manufacturing facility's through-put and may result in the processing of an adulterated blend out of specification. To increase production through-put and reduce segregation and de-mixing, blends may be compressed "at risk" before laboratory results are generated. However, if a finished product was compressed at risk and found to be out of specification with regard to blend uniformity, the batch may be rejected.

The present invention overcomes the major drawbacks associated with current sampling and analysis practices by way of a sampler device integrated with a NIRS fiber optic probe. An advantage of the present invention is that NIRS data acquisition can be performed immediately after sampling. Thus, the need to compress at risk or store blends for extended periods of time is eliminated. Because an external laboratory analysis is not required, an increase in laboratory capacity results from utilization of the fiber optic sampling device.

SUMMARY

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The purpose of the summary is to present some concepts of the invention in simplified form as a prelude to the more detailed description that is presented later.

In one embodiment, a sampling device, such as a grain-type device, is integrated with a probe to collect data from a sample, while contained in the sample chamber of the sampling device. For example, the probe can be a NIRS fiber optic probe used to perform analytical methods such as, inter alia, direct determination of blend uniformity.

In another embodiment, a sampling device includes an inner housing and an outer housing, wherein the outer housing surrounds a portion of the inner housing, a sample chamber for collecting a sample, wherein the sample chamber is a hollow cavity within the outer housing, and a probe within the inner housing configured to collect data from the sample. A portion of the internal surface of the sample chamber can have a low-reflectance finish. Further, the probe can be a NIRS fiber optic probe configured to transmit an NIR beam into the sample chamber.

In yet another embodiment, a sampling device includes an inner housing and an outer housing, wherein the outer housing surrounds a portion of the inner housing, a sample chamber for collecting a sample, wherein the sample chamber is a cavity of a slug positioned within the outer housing, and a probe within the inner housing configured to collect data from the sample. The slug is not positioned within the inner housing. A portion of an internal surface of the sample chamber comprises a low-reflectance finish. Further, the probe can be a NIRS fiber optic probe configured to transmit an NIR beam into the sample chamber.

BRIEF DESCRIPTION OF THE DRAWINGS

An example embodiment that incorporates one or more aspects of the present invention is described and illustrated in the following figures. The illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention.

FIG. 2A is a schematic view of an inner tube and a slug for use with a sampling device.

FIG. 2B is a cross-sectional view of the inner tube of FIG. 2A.

FIG. 3A is a schematic view of a slug for insertion into the outer housing of a sampling device.

FIG. 3B is a cross-sectional view of the slug of FIG. 3A.

DETAILED DESCRIPTION

As described herein, the sampling device can be made of pharmaceutically acceptable material for use in pharmaceutical applications, for example, the pharmaceutically acceptable material can be a suitable non-reactive material such as pharmaceutical grade stainless steel or a polymeric material. The sampling device is preferably made of material that provides rigidity to the device sufficient to withstand entering a powder or blend without bending so much as to damage the data collection probe contained therein. Material thickness can be selected as desired to maintain structural integrity and rigidity.

In one embodiment, the sampling device includes an inner housing and an outer housing, wherein a portion of the outer housing surrounds a portion of the inner housing. The device further includes a sample chamber for collecting a sample, wherein the sample chamber can be a hollow cavity within the outer housing, and a probe within the inner housing configured to collect data from the sample. The sample chamber can be a cavity within a removable slug that can be positioned within the outer housing. To provide access to the sample chamber, the outer housing can have an aperture and the slug can include an opening. The inner housing and the outer housing can be moveable relative to each other, for example in a rotating manner, to align the outer housing aperture and slug opening such that the sample chamber is open to an environment exterior to the outer housing through the slug opening and outer housing aperture. The outer housing can further include a handle. For example, the operator of the sampling device can utilize the handle to rotate the outer tube, align the aperture and opening, and expose the sample chamber for collecting a sample. A portion of the internal surface of the sample chamber can have a low-reflectance finish or coating and a NIRS fiber optic probe configured to transmit an NIR beam into the sample chamber for acquiring characteristic data of a sample.

Figure 1:
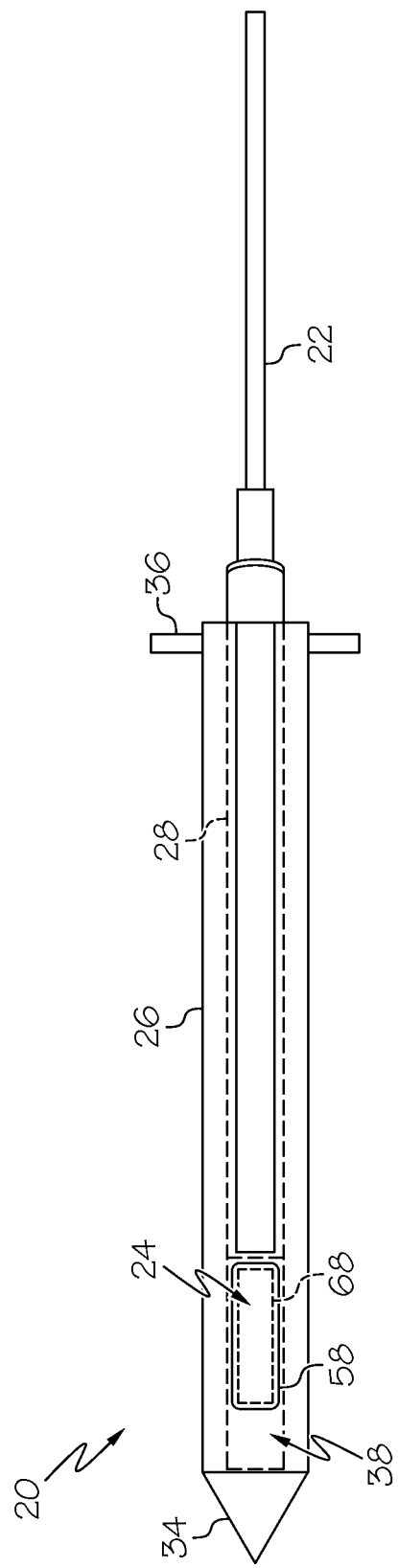
FIG. 1 is a schematic view of a sampling device incorporated with a fiber optic probe.

In one embodiment, referring now to FIG. 1, a sampling device 20 can include a NIRS fiber optic probe 22. As an advantage, NIRS data collection and analysis can be performed within the sampling device 20 simultaneously with or immediately after sampling, such that the sampled powder or blend need not be removed from the sample chamber 24. In an example, NIRS data collection can occur while the sampling device 20 is positioned in the blend or mixture being sampled. Data acquisition and blend uniformity results may be generated for each sample quickly, for example within 60 seconds or less. As such, the data acquisition and blend uniformity results may be generated for various sample locations of a powder bed within a short time frame, for example within 30 minutes or less. Various probe types and spectroscopy platforms can be used with the sampling device 20. In one embodiment, the data collection probe is a NIRS fiber optic probe 22 configured to transmit an NIR beam into the sample chamber 24 to analyze the sample.

As shown in FIG. 1, the sampling device 20, such as a grain-type sampling device, can include an outer housing, such as outer tube 26. The outer tube 26 can be open at one end and closed or capped at the opposite end, for example, a closed conical tip 34 is located at one end of the outer tube 26 which can lead the sampling device 20 as it is inserted inward to penetrate a powder or blend to be sampled. The outer tube 26 can have an open cavity section that extends uniformly from the open end to the closed end, the cavity adapted for receiving or accommodating an inner housing, such as inner tube 28 and/or a NIRS fiber optic probe 22, and a slug 38 containing a sample chamber 24. The closed end of the outer tube 26 provides a stop for the slug 38 to rest on, which in turn provides a stop for the inner tube 28 to rest on as the inner tube 28 is in direct contact with the slug 38. The outer diameter of the outer tube 26 can be in the range of 1 to 3 inches. The inner tube 28 and outer tube 26 are preferably cylindrical in shape. As shown, the inner tube 28 and outer tube 26 can be positioned in a concentric tube arrangement with the inner tube 28 nested inside the outer tube 26, wherein the tubes 26, 28 are movable with respect to one another.

The concentric tube arrangement allows the inner and outer tubes 28, 26 to freely rotate independent of one another. To aid rotation by a user, as shown, the outer tube can have an external handle 36 near the open end to aid in twisting the outer tube 26 during sampling procedures. Preferably, the inner tube 28 and outer tube 26 are positioned close enough to each other so as to prevent powder blend from entering the cavity or open space between them, but far enough apart so that rotation may occur. For example, the gap between the outer diameter of the inner tube 28 and the inner diameter of the outer tube 26 can be in the range of 0.1 to 0.4 inches or about 0.25 inches.

The length of the sampling device 20 can vary depending on the size of the vessel containing the powder or blend to be sampled, for example the sampling device 20 can be three to eight feet long or can be segmented in to achieve a desired length. In one embodiment, the sample is a powder. For example, the powder can comprise a pharmaceutical ingredient. Preferably, the components of the sampling device 20 are made from nonreactive material. For example, the nonreactive material can be stainless steel or a polymeric material.

As shown, the sample chamber 24, when empty, can be a hollow cavity within a removable slug 38 within the outer tube 26. The walls of the sample chamber 24 may exist in any form, for example rounded or squared. For example, the sample chamber 24 can have a rectangular cavity shape with substantially flat surfaces defining the shape (side walls and bottom). The top wall of the sample chamber 24 can be formed by the inner diameter surface of the outer tube 26. In an alternative example, the sample chamber 24 can be rounded, such as in a cylinder cavity shape wherein the side walls are rounded with a curvature similar to the outer and/or inner diameter of the inner tube 28. The volume of the sample chamber 24 can be adjustable. For example, the dimensions of the sample chamber 24 can vary depending on the size of the sample for which a particular sampling device is designed to obtain. For example, the operator of the sampling device 20 can select a removable slug 38 from multiple options, each containing a differently sized sample chamber 24, and the selected slug can be inserted and removed from the outer tube 26 to modify the sample size accordingly. In another embodiment, the size of the sample chamber 24 can be adjusted by placing one or more inserts (not shown) into the sample chamber 24 in order to reduce the volume of sample which can enter the chamber.

The slug 38 can be made of a suitable non-reactive material. For example, the slug 38 can be made from pharmaceutical grade stainless steel. In an alternative embodiment, the slug 38 can be made from a pharmaceutically acceptable plastic or polymer material. For example, if the slug 38 is made from a pharmaceutically acceptable plastic or polymer material, the material can be tinted or dark in color, such as blue in color to provide a non-reflective surface. In one embodiment, the plastic or polymer material is polyethylene.

Figure 4A:
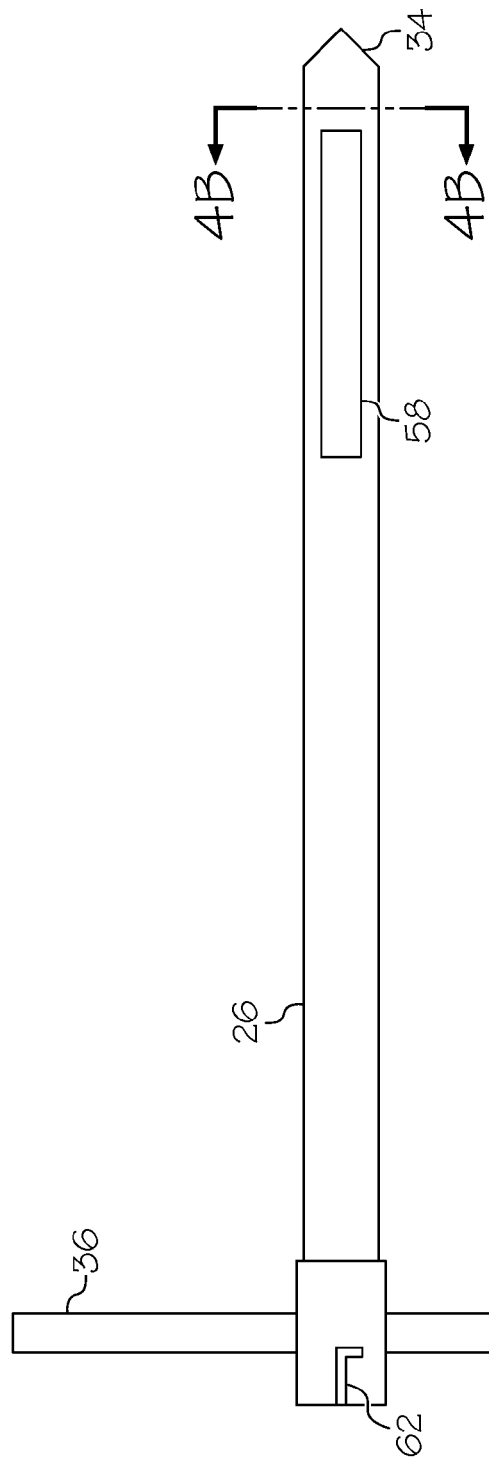
FIG. 4A is a schematic view of an outer tube for use with a sampling device.
Figure 4B:
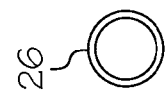
FIG. 4B is a cross-sectional view of the outer tube of FIG. 4A.

During use, the sample chamber 24 can be selectively opened and closed by the operator of the sampling device 20. For example, the slug 38 can have an opening 68, which when aligned with an aperture 58 of the outer tube 26, creates a pass-through opening for accommodating powder flow into the sample chamber 24. When the outer tube aperture 58 and slug opening 68 are not aligned, such that no access to the sample chamber 24 is provided, the sample chamber 24 is in the closed position and no powder can travel into the chamber. As shown in FIG. 2A and FIG. 3A, the slug 38 can have a rectangular-shaped opening 68 to the sample chamber 24. Likewise, as shown in FIG. 4A, the outer tube 26 can have a rectangular-shaped aperture 58 in its tube wall near the closed end portion having a conical tip 34. Referring again to FIG. 1, when the slug 38 is situated within the outer tube 26, the opening in the slug is the open section of the sample chamber 24 facing the inner wall surface of the outer tube 26. Because the outer tube aperture 58 and the slug opening 68 are not visible to the operator while the sampling device 20 is inserted into the powder bed, it can be difficult for an operator to precisely align such openings having identical dimensions. The particular dimensions of the slug opening 68, and the outer tube aperture 58 can vary, for example, the outer tube aperture 58 and slug opening 68 can be equally sized, the aperture 58 in the outer tube can be larger than the opening 68 in the slug, or vice versa. As such, the operator of the sampling device 20 may achieve effective alignment to open the sample chamber 24 without the need for exact precision.

The inner tube 28 can include a pin for rotation 56, as shown in FIG. 2A, which is configured to enter a slot for rotation 62, as shown in FIG. 4A, located on the outer tube 26. The handle 36, pin for rotation 56, and slot for rotation 62 enable the operator of the sampling device 20 to rotate the outer tube 26 such that the sample chamber 24 positioned within the outer housing is opened to an exterior environment outside the outer tube 26. The pin for rotation 56 and slot for rotation 62 can be arranged to guide the user for opening and closing the sample chamber 24 without having to view the rotating aperture in the outer tube.

Figure 5A:
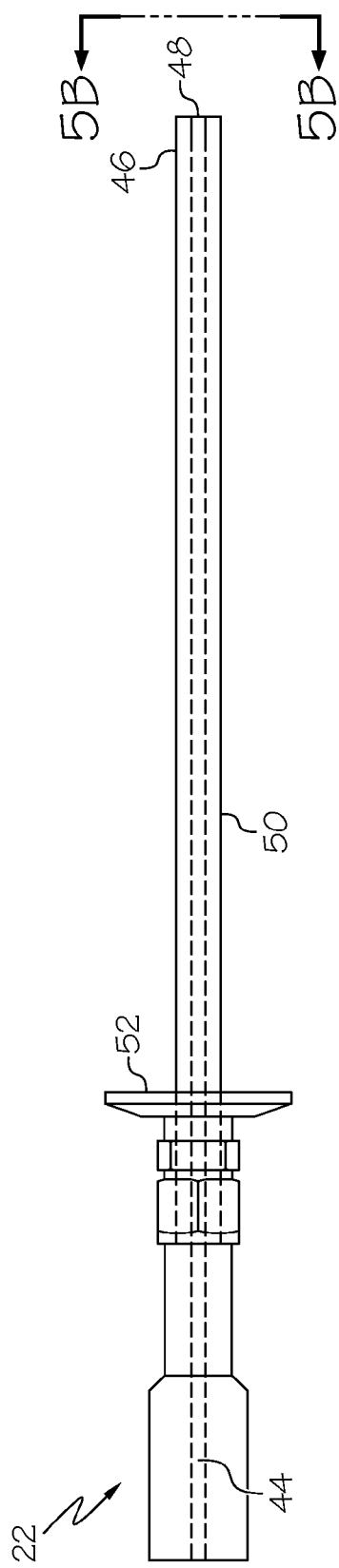
FIG. 5A is a schematic view of a fiber optic probe.
Figure 5B:
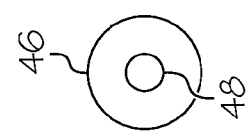
FIG. 5B is a cross-sectional view of the tip of the fiber optic probe of FIG. 5A.

The sample chamber 24 can have an opening along its surface, such as in a side wall, to accommodate a NIRS fiber optic probe 22. For example, the side wall of the sample chamber 24 facing an open end of the inner tube 28 can include an opening that connects the open cavity portion of the inner tube 28 with the sample chamber 24. In one embodiment, an internal surface of the sample chamber 24 comprises a portion of the probe. For example, the NIRS fiber optic probe body, as shown in FIG. 5A, can be inserted through an open cavity portion of the inner tube 28 of the grain-type sampler device such that the NIRS fiber optic probe tip 46, in particular the surface (window) 48, is positioned to form a wall of the sample chamber 24. Preferably, the NIRS fiber optic probe 22 is positioned such that the collected powder or blend sample, within the sample chamber, is in contact with the surface (window) 48 of the NIRS fiber optic probe tip 46. For example, the probe tip 46 fits in and fills the opening in the sample chamber side wall to create a sample chamber side wall surface free of open cracks or a pass through. The surface (window) 48 of the probe tip 46 can be made from NIR transparent material designed to prevent disruption of the NIRS beam. For example, the NIRS fiber optic probe tip surface (window) 48 is made from NIRS transparent material such as quartz or sapphire.

Securing the NIRS fiber optic probe 22, so that the glass surface (window) 48 of the probe tip forms a wall of the sample chamber, seals one end of the chamber and maximizes contact between the probe tip surface (window) 48 and the direct blend. In one embodiment, the NIRS probe is held in place and fastened to the inner tube 28 by an appropriate fastener, for example, by a compression fitting. In one embodiment, the NIRS probe 22 can include a first collar and the inner tube 28 can include a second collar, both of which can be removably attached to one another. For example, the NIRS probe collar 52, as shown in FIG. 5A, and the inner tube collar 54, as shown in FIG. 2A, may be removably attached to one another by a tri clamp fitting (not shown).

Referring again to FIG. 5A, the NIRS fiber optic probe 22 can include optical fibers 44 within a probe housing. For example, the probe housing can be a stainless steel tube. In one embodiment, the optical fibers 44 terminate at the NIRS probe collar 52. In this embodiment, the NIRS beam is directed through the stainless steel tube and enters the sample chamber 24 via the transparent NIRS probe tip surface (window) 48 for data collection. The remaining portion of the NIRS fiber optic probe 22, located outside of the sampling device, can be connected to an external coupling box. For example, the coupling box can send and receive signals from the NIRS unit located within the sampling device 20. In one embodiment, the NIRS fiber optic probe 22 is commercially available. For example, the NIRS fiber optic probe can be a Solvias fiber optic probe.

A portion of the internal surface of sample chamber 24 can be coated or adapted with a low-reflectance finish. The low-reflectance finish beneficially reduces or eliminates the amount of reflection of the NIRS beam from the sample chamber surface which may otherwise interfere with NIRS data acquisition and create errors in readings. The low-reflectance finish can be, for example, an anodic oxide finish created with an anodizing process as known in the art.

The sampling device 20 can be inserted into a powder bed at a point beyond the sample location with the sample chamber 24 in the closed position. Once the portion of the sampling device 20 where the sample chamber 24 is located is submerged in the bulk powder or blend, the sample chamber 24 is opened, for example by rotating the outer tube 26 and/or inner tube 28 to align the outer tube aperture 58 and slug opening 68 to expose the opening of the sample chamber 24 to the powder or blend. Opening the sample chamber 24 allows powder or blend to enter the sample chamber 24. After the desired volume of powder or blend sample enters the sample chamber 24, preferably the entire sample chamber 24 is filled, the operator closes the sample chamber 24 by similarly rotating the outer tube 26 and/or inner tube 28 to unalign the slug opening 68 and outer tube aperture 58 wherein the inner diameter surface of the outer tube forms the top wall of the sample chamber. NIRS data collection and analysis can be started by the operator once the sample chamber 24 is closed, either while the sample device 20 is located in the powder blend or mixture being sampled or when the device is removed from the tank or bed. In one embodiment, an operator performs both physical sample collection and NIRS data collection which allows determination of blend homogeneity of the sampled powder or blend. The sampling device 20 also provides investigational capability and the economic advantages include higher production throughput, higher laboratory capacity, reduction of out of specification batches, and compressing blends at risk. Therefore, an overall improvement in product quality can be realized.

The sampling device 20 can be disassembled for cleaning purposes. As such, the sampling device can meet criteria associated with GMP cleaning validations. Another feature of the sampling device is the optional inclusion of an internal air nozzle which provides in-line cleaning capability. In an embodiment where the device has an internal air nozzle, the sample chamber contains an additional opening for adaptation of the air nozzle. For example, the air nozzle can be secured flush with a wall of the sample chamber, positioned such that the air flow is directed at the surface of the data collection probe. In a preferred arrangement, the air nozzle can be part of the probe tip such that no openings in the sample chamber walls are needed. In another arrangement, the opening for the air nozzle can be on an adjacent wall to the wall containing the probe so the air can be directed towards the probe surface, perhaps at an angle. The outlet tip of the air nozzle should fit in and fill the entire opening to seal the wall surface in order to prevent powder from entering the sampling device outside of the sample chamber. This air flow can be used to remove any powder or blend sample that is sticking to the probe surface. The gas used in the air nozzle can be a nonreactive gas, for example nitrogen gas.

It will be apparent to those skilled in the art that various modifications and variations can be made without departing from the spirit and scope of the claimed invention.

We claim:
1. A sampling device comprising:
   a. an inner housing,
   b. an outer housing, the outer housing surrounding a portion of the inner housing, the outer housing having a closed end and an aperture capable of aligning with an opening of a sample chamber of a removable slug, the closed end providing a stop for the inner housing,
   c. the sample chamber for collecting a sample, wherein the sample chamber is a cavity of the slug positioned within the outer housing and the internal surface of the sample chamber comprises a low-reflectance finish, the sample chamber opening connects the sample chamber with the inner housing, the slug having an opening to the sample chamber wherein the sample chamber may be selectively open to or closed off from the environment exterior to the outer housing, and
   d. a probe positioned within the inner housing, the probe having a probe tip that fits in the opening of the sample chamber, the probe configured to transmit an NIR beam into the sample and collect data from the sample.

2. The sampling device of claim 1, wherein the removable slug is not positioned within the inner housing.

3. The sampling device of claim 1, wherein the inner housing and the outer housing are moveable relative to each other to selectively align the aperture in the outer housing with the opening to the sample chamber opening such that the sample chamber is open to an environment exterior to the outer housing through the aligned opening and aperture.

4. The sampling device of claim 1, wherein an internal surface of the sample chamber comprises a portion of the probe.

5. The sampling device of claim 4, wherein the probe tip is in contact with the slug such that the tip of the probe forms an internal surface of the sample chamber.

6. The sampling device of claim 5, wherein the surface of the probe tip forms an internal surface of the sample chamber such that, when the sample chamber contains a sample the sample is in contact with the probe tip surface.

7. The sampling device of claim 1, wherein the probe is a NIRS fiber optic probe configured to transmit an NIR beam into the sample chamber to analyze the sample.

8. The sampling device of claim 7, wherein the NIRS fiber optic probe comprises a tip made from NIR transparent material, the tip being an internal surface of the sample chamber.

9. The sampling device of claim 8, wherein the NIRS transparent material is quartz or sapphire.

10. The sampling device of claim 8, wherein the tip of the NIRS fiber optic probe is in contact with the slug.

11. The sampling device of claim 1, wherein the outer housing further comprises a handle for moving the outer housing relative to the inner housing to expose the sample chamber to an environment exterior to the outer housing.

12. The sampling device of claim 1, wherein the sample chamber is not positioned within the inner housing.

13. The sampling device of claim 1, wherein the low-reflectance finish is an anodic oxide finish.

14. The sampling device of claim 1, wherein the sample chamber is made from nonreactive material.

15. The sampling device of claim 1, wherein the sample is a powder.

16. The sampling device of claim 15, wherein the powder comprises an active pharmaceutical ingredient.

17. A sampling device comprising:
   a. an inner housing,
   b. an outer housing, a portion of the inner housing positioned inside the outer housing, the outer housing having a closed end and an aperture capable of aligning with an opening of a sample chamber of a removable slug, the closed end providing a stop for the inner housing,
   c. the sample chamber for collecting a sample, wherein the sample chamber is a cavity of the removable slug positioned within the outer housing, the sample chamber opening connects the sample chamber with the inner housing, the removable slug having an opening to the sample chamber wherein the sample chamber may be selectively open to or closed off from the environment exterior to the outer housing, and wherein the internal surface of the sample chamber comprises a low-reflectance finish, and
   d. a NIRS fiber optic probe positioned within the inner housing, the NIRS probe having a probe tip that fits in the opening of the sample chamber, and the NIRS fiber optic probe configured to transmit an NIR beam into the sample chamber.

18. The sampling device of claim 17, the slug not being positioned within the inner housing.

* * * * *